US012721529B2

(12) United States Patent
Tang et al.

(10) Patent No.: US 12,721,529 B2
(45) Date of Patent: Sep. 1, 2026

(54) DEVICE AND METHOD FOR RAPID DETECTION OF BLOOD VISCOSITY BASED ON ULTRASONIC GUIDED WAVE OF MICRO-FINE METAL TUBE

(71) Applicant: ZHEJIANG UNIVERSITY, Hangzhou (CN)

(72) Inventors: Zhifeng Tang, Hangzhou (CN); Junwang Ma, Hangzhou (CN); Zhengyang Huang, Hangzhou (CN); Zhiyang Li, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 1070 days.

(21) Appl. No.: 17/796,053

(22) PCT Filed: Dec. 9, 2021

(86) PCT No.: PCT/CN2021/136673
§ 371 (c)(1),
(2) Date: Jul. 28, 2022

(87) PCT Pub. No.: WO2022/213645
PCT Pub. Date: Oct. 13, 2022

(65) Prior Publication Data
US 2023/0404410 A1 Dec. 21, 2023

(30) Foreign Application Priority Data
Apr. 8, 2021 (CN) ......................... 202110378292.2

(51) Int. Cl.
*A61B 5/02* (2006.01)
*G01N 11/04* (2006.01)

(52) U.S. Cl.
CPC .......... *A61B 5/02035* (2013.01); *G01N 11/04* (2013.01)

(58) Field of Classification Search
None
See application file for complete search history.

(56) References Cited

U.S. PATENT DOCUMENTS 4,893,496 A 1/1990 Bau et al.
6,796,168 B1 * 9/2004 Goldstein .............. G01N 11/04 73/54.04

(Continued)

FOREIGN PATENT DOCUMENTS

CN 102854090 A 1/2013
CN 108508085 A 9/2018
CN 113203661 A 8/2021

OTHER PUBLICATIONS

International Search Report, PCT/CN2021/136673, Mar. 10, 2022, 5 pages.

(Continued)

*Primary Examiner* — Daniel S Larkin

(57) ABSTRACT

A device and a method for rapid detection of blood viscosity based on an ultrasonic guided wave of a micro-fine metal tube are provided. The device comprises a blood sampling unit and a blood sampling electrical circuit that are electrically connected with each other and a device shell; the sample feeding tube and the sample discharging tube are respectively arranged at two sides of the device shell, the inlet of the sampling tube is communicated with the outside of the device shell, the outlet of the sampling tube is communicated with the inlet of the blood micro-flow pump through the micro-fine metal tube, the outlet of the blood micro-flow pump is communicated with the inlet of the sample discharging tube, and the outlet of the sample discharging tube is communicated with the outside of the device shell; the magnetostrictive component is arranged outside the micro-fine metal tube.

20 Claims, 5 Drawing Sheets

(56) References Cited

U.S. PATENT DOCUMENTS

| | | | |
|---|---|---|---|
| 2004/0065143 | A1 | 4/2004 | Husher |
| 2006/0010963 | A1 | 1/2006 | Bach et al. |
| 2015/0052981 | A1 | 2/2015 | Kim et al. |

OTHER PUBLICATIONS

Kong et al., "Influence of Viscous Liquid on Propagation of Torsional Wave in a Pipe," Journal of Vibration and Shock, vol. 31, No. 11, Nov. 30, 2012, ISSN: 1000-3835, pp. 48-53.

* cited by examiner

| Best parameters: $k_1, k_2$=[7.1560,8.8067] | | | |
|---|---|---|---|
| $Min_{MSN}$:0.00004 | | | |
| $k_1$ | $k_2$ | $\eta$ | $\eta_{predict}$ |
| 0.021 | 0.017 | 0.3 | 0.3008 |
| 0.043 | 0.033 | 0.6 | 0.6000 |
| 0.054 | 0.046 | 0.8 | 0.7936 |
| 0.066 | 0.049 | 0.9 | 0.9064 |

DEVICE AND METHOD FOR RAPID DETECTION OF BLOOD VISCOSITY BASED ON ULTRASONIC GUIDED WAVE OF MICRO-FINE METAL TUBE

CROSS REFERENCE TO RELATED APPLICATION

The present disclosure is a national stage application of International Patent Application No. PCT/CN2021/136673, filed on Dec. 9, 2021, which claims benefit and priority of the Chinese patent application entitled "DEVICE AND METHOD FOR RAPID DETECTION OF BLOOD VISCOSITY BASED ON ULTRASONIC GUIDED WAVE OF MICRO-FINE METAL TUBE" filed before the Chinese Patent Office on Apr. 8, 2021 with the application number of 202110378292.2, and the disclosure of which is incorporated by reference herein in its entirety in this disclosure.

TECHNICAL FIELD

The present disclosure relates to the technical field of blood viscosity detection, in particular to a device and a method for rapid detection of blood viscosity based on ultrasonic guided waves of a micro-fine metal tube.

BACKGROUND ART

Blood viscosity is one of the physicochemical properties of blood. Under an environment of 36° C., the viscosity of human whole blood is generally between 2.3-3.5 mPa·s. The viscosity of human whole blood is mainly related to RBC (packed cell volume, deformability of red blood cells, and aggregation of red blood cells), the content of hemoglobin and other proteins, plasma viscosity, and the like.

The detection of blood viscosity is of great significance in the field of biomedicine. Cardiovascular diseases, such as ischemic cerebral apoplexy, myocardial infarction, cerebral thrombosis and the like, are accompanied by the increase of blood viscosity (>4 mPa·s). Hemorrhagic cerebral apoplexy and digestive tract hemorrhage are also accompanied by the decrease of blood viscosity (<2 mPa s).

A blood viscometer is an instrument that measures the viscosity of human blood under physiological conditions. At present, most of blood viscosity analyses in hospitals are performed on blood samples drawn from patients, and, for example, a device for measuring dynamic viscosity of blood provided by BIHE SCIENTIFIC INSTRUMENT needs to add anticoagulant into the blood samples, centrifuge the blood samples with anticoagulant for 3 minutes in a machine, and then take the centrifuged samples for analysis and test, wherein the whole working period is about 15 minutes. This type of detection instrument has poor real-time performance, and it is necessary to ensure that the blood samples are not affected by external factors, such as air and temperature, during the detection.

The real-time rapid measurement of the blood viscosity has more important significance in emergency treatment and emergency surgery situations, and the parameter can reflect the current physiological condition of a patient and further influence the formulation of a doctor's emergency plan for the patient. Ultrasonic guided wave measurement is favored by researchers due to the characteristics of high measurement speed, high precision and the like. The ZHAO Meirong team of Tianjin University applies the L-mode guided wave of a pipeline to the viscosity measurement of viscoelasticity liquids, which however is restricted by the capillary torsion guided wave sensor technology, and thus adopts the L-guided wave which is easy to be excited relatively. Under the condition that the diameter of the micro-fine metal tube is reduced, the change of the frequency dispersion curve of guided wave in the liquid-filled tube along with the change of the viscosity of the filled liquid is more obvious. Since the shear wave is more sensitive to the viscosity change of the liquid, how to excite the pure T (0, 1) mode capillary guided wave is the key to further improve the accuracy of viscosity measurement.

SUMMARY

To solve the problems of low speed and low real-time property of detection of the blood viscosity of a human body, the present disclosure provides a device for directly collecting and measuring blood in real time by utilizing the characteristic that the torsional mode ultrasonic guided wave propagation in a micro-fine metal tube is influenced by a fluid shearing force, and the device is suitable for medical units to quickly detect the blood viscosity of patients.

The disclosure relates to a device based on the rule that the dispersion curve and the amplitude attenuation of the ultrasonic guided wave propagation on the inner surface of the micro-fine metal tube are affected by the viscosity of the liquid in the tube, for predicting blood viscosity by performing regression analysis on blood viscosity by using a machine learning method and drawing a (W (guided wave attenuation parameter) according to the time of flight and amplitude of the measured guided wave echo as variables. ΔTOF (absolute time of flight)-viscosity curve was used to predict blood viscosity, and a device for rapidly sampling and detecting the blood of a human body matching with the method is designed. The portable ultrasonic guided wave exciting device and the micro-fine metal needle tube excite torsional mode (T mode) guided wave, and blood is directly collected through the micro-fine metal needle tube. The blood is ensured not to contact with air during testing, and the precision of blood viscosity measurement is improved by keeping constant the temperature of the needle tube and the length of the liquid column and other influencing factors.

The disclosure is realized by the following technical solutions:

- a device for rapid detection of blood viscosity in a micro-fine metal tube based on torsional guided waves comprises:
- a device shell, a blood sampling unit and a blood sampling circuit, wherein the blood sampling unit and the blood sampling circuit are arranged on the device shell and are electrically connected to each other; the blood sampling unit comprises an external blood sampling module, a sample transportation pipeline, a micro-fine metal tube and a blood micro-flow pump, wherein the sample transportation pipeline comprises a sample feeding tube and a sample discharging tube, the sample feeding tube and the sample discharging tube are respectively arranged on two sides of a device shell, the inlet of the sample feeding tube is communicated with the outside of the device shell and is used for being connected with the external blood sampling module, the outlet of the sample feeding tube is communicated with the inlet of the blood micro-flow pump through the micro-fine metal tube, the outlet of the blood micro-flow pump is communicated with the inlet of the sample discharging tube, and the outlet of the sample discharging tube is communicated with the outside of the device shell; a magnetostrictive component is arranged outside the micro-fine metal tube and comprises permanent magnets, a coil and a magnetostrictive powder coating, the magnetostrictive powder coating is coated on an outer surface of the micro-fine metal tube, the coil is wound outside the magnetostrictive powder coating, and the permanent magnets are symmetrically arranged on two sides outside the coil.

The external blood sampling module comprises a sampling needle and a blood sampling bag, the blood sampling bag is connected with the sample feeding tube, and the blood sampling bag is configured for sampling blood in veins of a human body through the sampling needle.

The blood micro-flow pump and the coil are connected to a blood sampling electrical circuit, and the blood sampling electrical circuit comprises a main control unit, a guided wave excitation unit, a pulse generation module, a power amplification module, an echo receiving unit, a pre-amplification module and a data acquisition module; the main control unit is connected with the display module, the main control unit is connected with the blood micro-flow pump through the micro-flow pump control module, the main control unit is connected with two ends of the coil through the guided wave excitation unit, the pulse generation module and the power amplification module in sequence, and the two ends of the coil are connected with the main control unit through the data acquisition module, the pre-amplification module and the echo receiving unit in sequence.

The main control unit arranges an original excitation pulse digital signal and then sends the digital signal to the guided wave excitation unit, the digital signal is converted into an analog signal by the pulse generation module, the analog signal is amplified by the power of the power amplification module and then applied to a guided wave transducer formed by a coil and permanent magnets, and the guided wave signal is coupled to the micro-fine metal tube by the guided wave transducer; when the guided wave transducer receives the echo of the guided wave, the received echo signal is sent to the main control unit for data processing after being subjected to pre-amplification by the data acquisition module and the pre-amplification module in sequence, and the result is displayed on the display module after the viscosity is predicted by a detection method.

Secondly, a method for detecting blood viscosity based on machine learning comprises:

1) calculating by a semi-analytic finite element method to obtain a dispersion characteristic curve of guided wave modal of the liquid-filled micro-fine metal tube according to structural geometric parameters and material mechanics characteristic parameters of the micro-fine metal tube, and selecting guided wave excitation frequency according to the dispersion characteristic curve of guided wave modal, determining that the variation of T (0, 1) mode guided wave propagation speed in the liquid-filled metal tube with different viscosities is large through the dispersion characteristic curve of guided wave modal, and the velocity change sensitivity of the excited guided wave near 240 khz is higher and further away from the cut-off frequency;
2) taking water at 36° C. as a solvent, using a thickening agent as a solute, preparing liquids with different concentrations to obtain liquids with different viscosities, and measuring the viscosities of the prepared liquids by using a commercial standard viscometer to obtain actual viscosities;
3) filling liquid with different viscosities into the micro-fine metal tube, obtaining time of flight TOF and amplitude AMP of guided wave in the micro-fine metal tube (5) by acquiring and then processing echo signals under the guided wave excitation of T (0, 1) guided wave excitation frequency, and then calculating absolute time of flight ΔTOF and amplitude attenuation ratio w according to the time of flight TOF and amplitude AMP of guided wave;
guided wave time of flight (TOF) is calculated from the reciprocal of the guided wave velocity, and Amplitude (AMP) is the maximum amplitude of the echo;
4) According to the relation between the absolute time of flight ΔTOF and the amplitude attenuation ratio w and the viscosity found by experiments, establishing a linear regression model among the absolute time of flight ΔTOF, the amplitude attenuation ratio w and the viscosity, the linear regression model predicts two input variables of the absolute time of flight ΔTOF and the amplitude attenuation ratio w to obtain predicted viscosity, establishing loss function measurement according to the difference between the predicted viscosity and the actual viscosity, using the linear regression model in supervised learning to map the input variables to the viscosity and using the gradient descent optimization method to optimize the model can effectively enhance and correct the loss function;
the linear regression model has the inputs of absolute time of flight ΔTOF and amplitude attenuation ratio w, and the output is viscosity;
5) adding the blood sample into a micro-fine metal tube under a condition of to be detected, repeating steps 3) and 4) to obtain the absolute time of flight ΔTOF and the amplitude attenuation ratio w, input the absolute time of flight ΔTOF and the amplitude attenuation ratio w into a linear regression model in supervised learning and output an obtained viscosity, and optimize the model by using a gradient descent optimization method.

In the step 1), the guided wave modal is a T (0, 1) modal guided wave, and is a torsional wave of the T (0, 1) modal, which is more sensitive to a liquid shearing force, and the propagation characteristic is greatly influenced by viscosity.

According to the dispersion characteristic curve of the micro-fine metal tube in the step 1), when the viscosity of filled liquid in the micro-fine metal tube is increased, the dispersion curve displaces to the right, which indicates that with the same frequency, a propagation speed of a guided wave in an inner wall of the micro-fine metal tube is higher when the viscosity of filled fluid is larger, and the time of flight TOF of the guided wave is shorter.

The solute thickener used in the step 2) is hydroxyethyl cellulose (HEC) powder, has little influence on the liquid density, and the viscosity of a 1% HEC solution can reach 397 mPa·s and the density is only 1.005 g/cm$^3$.

In a specific implementation, the micro-fine metal tube is a metal aluminum tube or a stainless steel tube or the like.

In the step 3), echo signals are collected to obtain guided wave propagation velocity v, and in turn time of flight TOF of guided wave is obtained by processing according to the guided wave propagation velocity and the length of the micro-fine metal tube in the following mode:

$$TOF=2\times l/v$$

wherein, TOF is the time of flight of guided wave, l is the length of the micro-fine metal tube, and v is the guided wave propagation speed of the guided wave inside the micro-fine metal tube.

In the step 4), the linear regression model specifically is:

$$\eta=k_1*\Delta TOF+k_2*w$$

wherein k1 and k2 are a first model coefficient and a second model coefficient, and η represents viscosity;

the loss function uses the mean square error as the function return value, and is calculated as:

$$J = \frac{1}{2}\sum_{i=1}^{m}(h(x^i) - y^i)^2$$

wherein J represents the mean square error between the predicted viscosity and the actual viscosity, is the predicted viscosity obtained by processing the absolute time of flight ΔTOF and the amplitude attenuation ratio w through the linear regression model, $y^i$ is the actual viscosity of the solution prepared by using a standard viscometer, i represents the ith HEC powder solution, and m represents the total parts of the HEC powder solution.

The present disclosure realizes blood collection and rapid viscosity measurement by constructing the portable blood viscosity rapid detection device and utilizing the rule that the echo characteristic of the ultrasonic guided wave changes along with the blood viscosity, the blood temperature is constant by using the constant-temperature heating module, and the analyzed guided wave flight time and amplitude are sent to the trained viscosity calculation model, so that the blood viscosity measurement speed and accuracy are improved, and the problem of poor real-time performance/slow detection speed of the traditional blood viscosity detection device is solved.

The device can realize the detection of the blood viscosity in the shortest time according to the echo characteristics after the blood viscosity is collected by modeling the guided wave echo characteristics in the blood viscosity interval of the human body, has a high integration level and small volume, is easy to carry, can directly display the measured blood viscosity on the display interface of the device, and can help medical personnel to conveniently obtain the blood viscosity data of the patient.

The disclosure has the following beneficial effects.

The device of the present disclosure for directly collecting and measuring the blood viscosity in real time overcomes the problems that the traditional blood viscosity measurement has poor real-time performance and overlarge collection amount, cannot be used in the occasions of surgery and first aid, is easy to cause larger errors by environmental factors in the measurement process and the like.

The present disclosure utilizes the characteristic that the blood fluid shearing force influences the transmission of the torsional mode ultrasonic guided wave in the inner wall of the micro-fine metal tube, extracts the time of flight data and the amplitude attenuation data in the torsional guided wave echo, and utilizes machine learning to predict the blood viscosity, thereby realizing the real-time and accurate measurement of the blood viscosity.

The method has high accuracy, can make quick calculation and display the blood viscosity after the blood sampling device collects blood into the micro-fine metal tube, has small blood sampling amount and convenient sampling, and is suitable for quick real-time detection of the blood viscosity of a patient in a medical unit.

BRIEF DESCRIPTION OF THE DRAWINGS

In order to more clearly illustrate the embodiments of the present invention or the technical solutions in the prior art, the drawings required in the embodiments will be briefly described below, and it is obvious that the drawings in the following description are only some embodiments of the present invention, and it is obvious for those skilled in the art that other drawings can be obtained according to these drawings without creative efforts.

FIG. 3*a* is a diagram showing the variation of dispersion curve of the liquid-filled metal tubes with different viscosities;

FIG. 3*b* is a diagram showing the variation of the echo velocity of liquid-filled metal tubes with different viscosities;

FIG. 3*c* is a diagram showing the variation of the echo amplitudes of the liquid-filled metal tubes with different viscosities;

In the figures: 1—shell, 2—sampling needle; 3—blood sampling bag; 4—sample feeding tube; 5—micro-fine metal tube; 6—sample discharging tube; 7—micro-pump; 8—main control unit; 9—display module; 10—micro-flow pump control module; 11—guided wave excitation unit; 12—pulse generating module; 13—power amplification module; 14—echo receiving unit; 15—pre-amplification module; 16—data acquisition module; 17—permanent magnet; 18—coil; 19—magnetostrictive powder coating.

DETAILED DESCRIPTION OF THE EMBODIMENTS

The technical solutions in the embodiments of the present disclosure will be clearly and completely described below with reference to the drawings in the embodiments of the present disclosure, and it is obvious that the described embodiments are only a part of the embodiments of the present disclosure, and not all of the embodiments. All other embodiments, which can be obtained by a person skilled in the art without making any creative effort based on the embodiments in the present disclosure, belong to the protection scope of the present disclosure.

Figure 1:
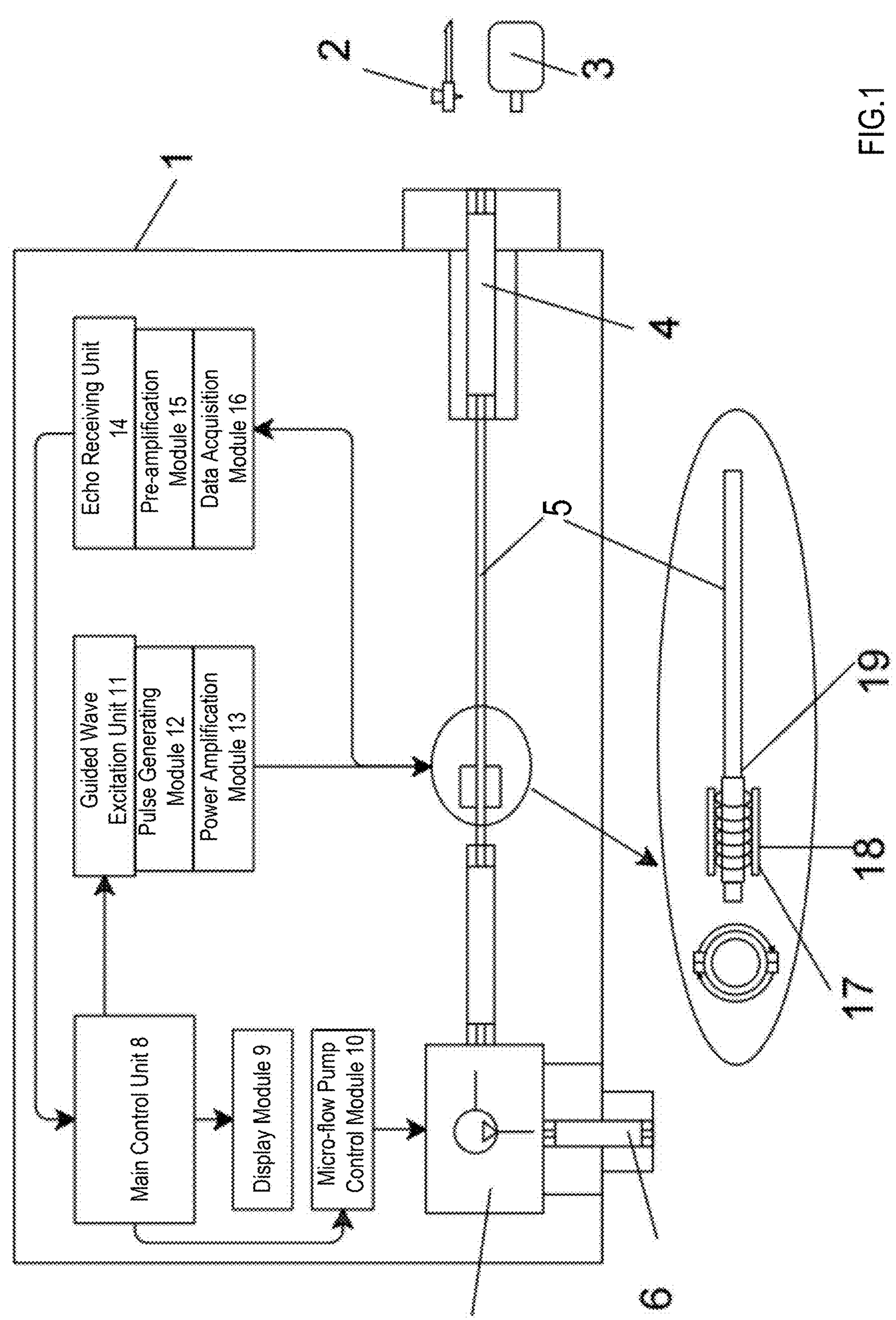
FIG. 1 is a view of the composition structure of a blood viscosity measuring device.
Figure 2:
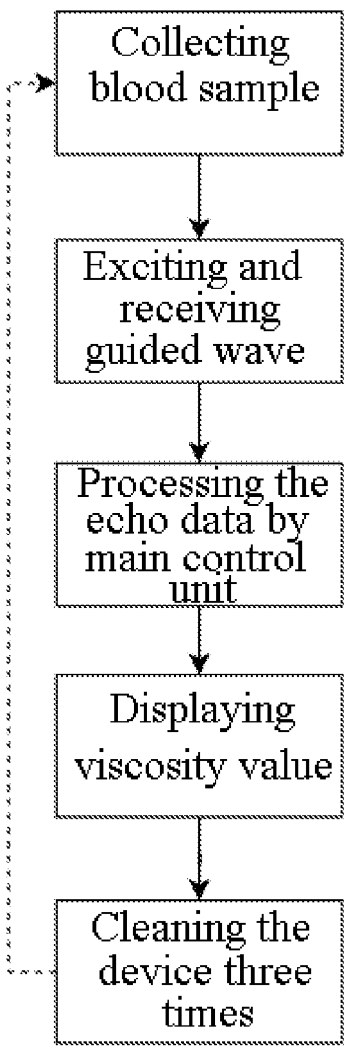
FIG. 2 is a flow chart of the operation of the blood viscosity measuring device.

As shown in FIG. 1, the device includes a device shell 1, and a blood sampling unit and a blood sampling electrical circuit mounted to the device shell, the blood sampling unit and the blood sampling electrical circuit being electrically connected to each other.

The blood sampling unit comprises an external blood sampling module, a sample transportation pipeline, a micro-fine metal tube 5 and a blood micro-flow pump 7, the external blood sampling module is connected with a disposable blood sampling needle 2 or a collected blood sample, and the blood micro-flow pump 7 is configured for controlling blood to be sucked and sending the blood into the micro-fine metal tube 5 for detection. After the detection is completed, the blood sample in the micro-fine metal tube 5 is sent out through the sample transportation pipeline and washed three times by distilled water.

The sample transportation pipeline comprises a sample feeding tube 4 and a sample discharging tube 6, the sample feeding tube 4 and the sample discharging tube 6 are respectively arranged at two sides of the device shell, the inlet of the sample feeding tube 4 is communicated with the outside of the device shell and is used for connecting an external blood sampling module, the outlet of the sample feeding tube 4 is communicated with the inlet of the blood micro-flow pump 7 through the micro-fine metal tube 5, a rubber hose, the outlet of the blood micro-flow pump 7 is communicated with the inlet of the sample discharging tube 6, and the outlet of the sample discharging tube 6 is communicated with the outside of the device shell; the sample transportation pipeline and the micro-fine metal tube 5 are fixed in the device shell. The diameter range of the micro-fine metal tube 5 is 0.1 mm-2 mm, and the length is 5 mm-50 mm.

The sample transportation pipeline is a rubber hose, is connected with the inlet of the device shell and the two sides of the blood micro-flow pump 7, and can be replaced.

A magnetostrictive component is arranged outside the micro-fine metal tube 5, the magnetostrictive component comprises permanent magnets 17, a coil 18 and a magnetostrictive powder coating 19, the magnetostrictive powder coating 19 is coated on the outer surface of the micro-fine metal tube 5, the coil 18 is wound outside the magnetostrictive powder coating 19, and the permanent magnets 17 are symmetrically arranged on two sides outside the coil 18.

One side of the circumference of the micro-fine metal tube 5 is plated with a layer of magnetostrictive powder to form the magnetostrictive powder coating 19, and the circumference is wrapped with a magnetostrictive torsional waveguide transducer which consists of a magnet and a coil, wherein two magnets are used as permanent magnets 17 to provide a permanent magnetic field, and a pulse echo mode is utilized to carry out guided wave excitation and reception.

The diameter range of the micro-fine metal tube 5 is 0.1 mm-2 mm, the length is 5 mm-50 mm, a ferromagnetic tube (such as a carbon steel tube and a stainless steel tube) or a non-ferromagnetic tube (such as an aluminum tube and a copper tube) is used, the magnetostrictive powder coating is sprayed on the non-ferromagnetic tube to transmit T (0,1) guided waves, the ferromagnetic tube can transmit T (0,1) modal guided waves, and the guided waves are more favorably transmitted in the micro-fine metal tube after the magnetostrictive powder coating is sprayed.

The magnetostrictive powder coating material is FeCo, FeGa, NiMnGa or Terfelnol-D and the like, and the magnetostrictive powder spraying process adopts an ultrasonic cold spraying or hot spraying process.

The external blood sampling module comprises a sampling needle 2 and a blood sampling bag 3, the blood sampling bag 3 is connected with a sample feeding tube 4, and the blood sampling bag 3 is used for sampling blood in veins of a human body through the sampling needle 2. The collection modes include blood collection by direct venous blood taking needle and blood collection by blood samples of blood collection bags.

The external blood sampling module can directly carry out detection on the blood sampling and feeding device for veins of a human body when being connected with the disposable blood sampling needle, and can carry out blood sampling firstly and then feed the blood into the device when being connected with a blood sample.

The blood micro-flow pump 7 and the coil 18 are connected to a blood sampling electrical circuit, and the blood sampling electrical circuit comprises a main control unit 8, a guided wave excitation unit 11, a pulse generation module 12, a power amplification module 13, an echo receiving unit 14, a pre-amplification module 15 and a data acquisition module 16; the main control unit 8 is connected with the display module 9, the main control unit 8 is connected with the blood micro-flow pump 7 through the micro-flow pump control module 10, the main control unit 8 is connected with two ends of the coil 18 through the guided wave excitation unit 11, the pulse generation module 12 and the power amplification module 13 in sequence, furthermore, two ends of the coil 18 are connected with the main control unit 8 through the data acquisition module 16, the pre-amplification module 15 and the echo receiving unit 14 in sequence. A guided wave excitation unit is mainly composed of a guided wave excitation device 11, a pulse generation module 12 and a power amplification module 13, and a guided wave receiving unit is mainly composed of a data acquisition module 16, a pre-amplification module 15 and an echo receiving unit 14.

The main control unit 8 arranges an original excitation pulse digital signal and then sends the signal to the guided wave excitation unit 11, the signal is converted into an analog signal by the pulse generation module 12, the analog signal is amplified by the power of the power amplification module 13 and then applied to a guided wave transducer formed by a coil 18 and a permanent magnet 17, and the guided wave signal is coupled to the micro-fine metal tube 5 by the guided wave transducer; when the guided wave transducer receives the echo of the guided wave, the received echo signal is sent to the main control unit 8 after passing the data acquisition module 16 and then being pre-amplified by the pre-amplification module 15 in sequence for data processing, and the result is displayed on the display module 9 after the viscosity is predicted by a detection method.

When a blood sample is filled in the micro-fine metal tube 5, the guided wave excitation unit receives a main control excitation signal and drives the transducer to generate ultrasonic guided waves, and in the pulse echo mode, the ultrasonic guided waves are excited to the metal tube through the guided wave excitation unit, then emitted at the edge of the metal tube, captured by the transducer in the process of back propagation, and sent to the guided wave receiving unit. In experimental exploration, the received guided wave has different propagation speed and amplitude when the blood viscosity is different.

The pulse echo mode is suitable for spraying magnetic powder and installing a guided wave transducer at one position of the metal tube, and the device can also be used for installing the guided wave transducer by spraying the magnetic powder at two positions of two sides and receiving the magnetic powder in a single-transmitting and single-receiving mode.

The device of the present disclosure can also realize dynamic detection of blood viscosity, and can draw a thrombelastogram by continuously collecting the change of the blood viscosity along with time and collecting the data of 50 groups of normal people to draw the thrombelastogram for comparison so as to determine human body thrombi, blood coagulation and the like through other corresponding indexes by plating kaolin clay on the wall of the micro-fine metal tube.

Figure 3A:
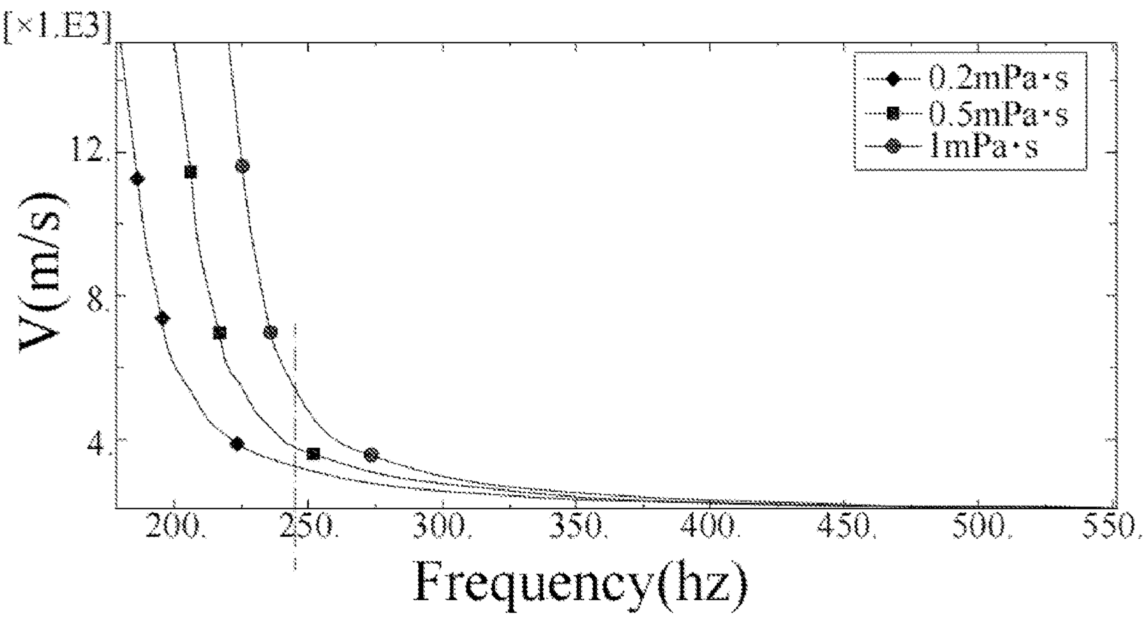
FIGS. 3*a*-3C are schematic diagrams of a method for rapidly measuring blood viscosity.

FIG. 3 shows a schematic diagram of the detection of blood viscosity, and the data of the diagram is from three sets of experiments simulating the change of blood viscosity, and the experimental conditions are as follows:

1. A stainless steel tube with a diameter of 0.6 mm and a length of 10 cm is sprayed with iron-cobalt magnetostrictive powder coating at a distance of 1 cm from one end.
2. The length of the liquid column was 10 cm, the temperature was 36° C., the density of the liquid column was 1.05 g/cm$^3$, and the viscosity of the liquid column is 0.1 mPa·s, 0.5 mPa·s, and 1 mPa·s, respectively.
3. The guided wave excitation frequency was 240 khz.

Figure 3B:
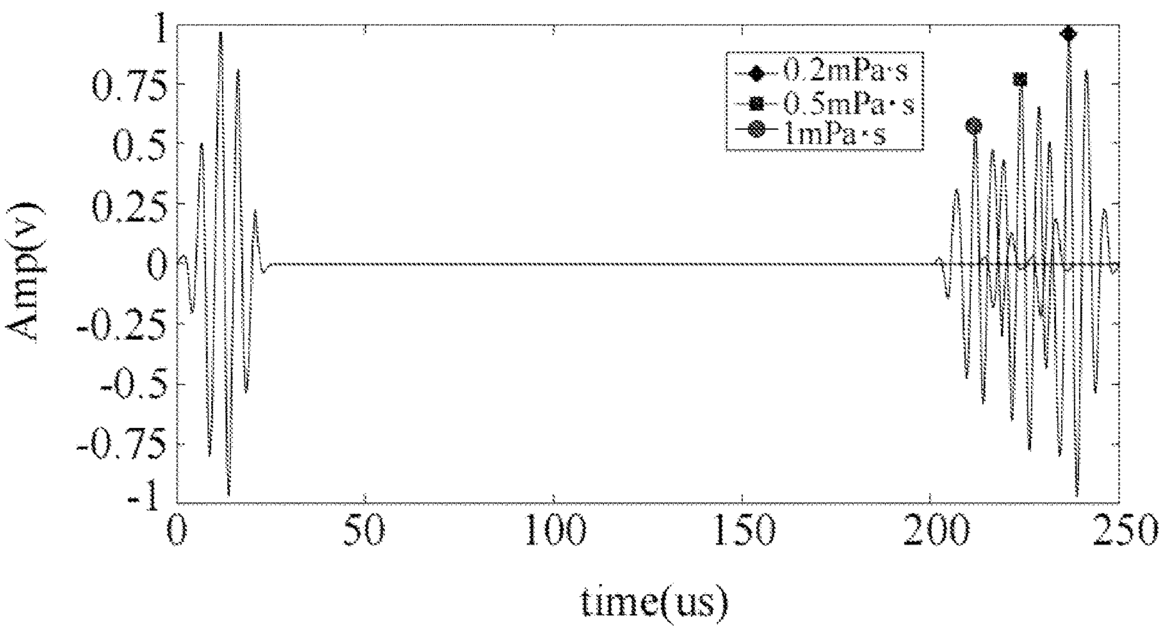
Figure 3C:
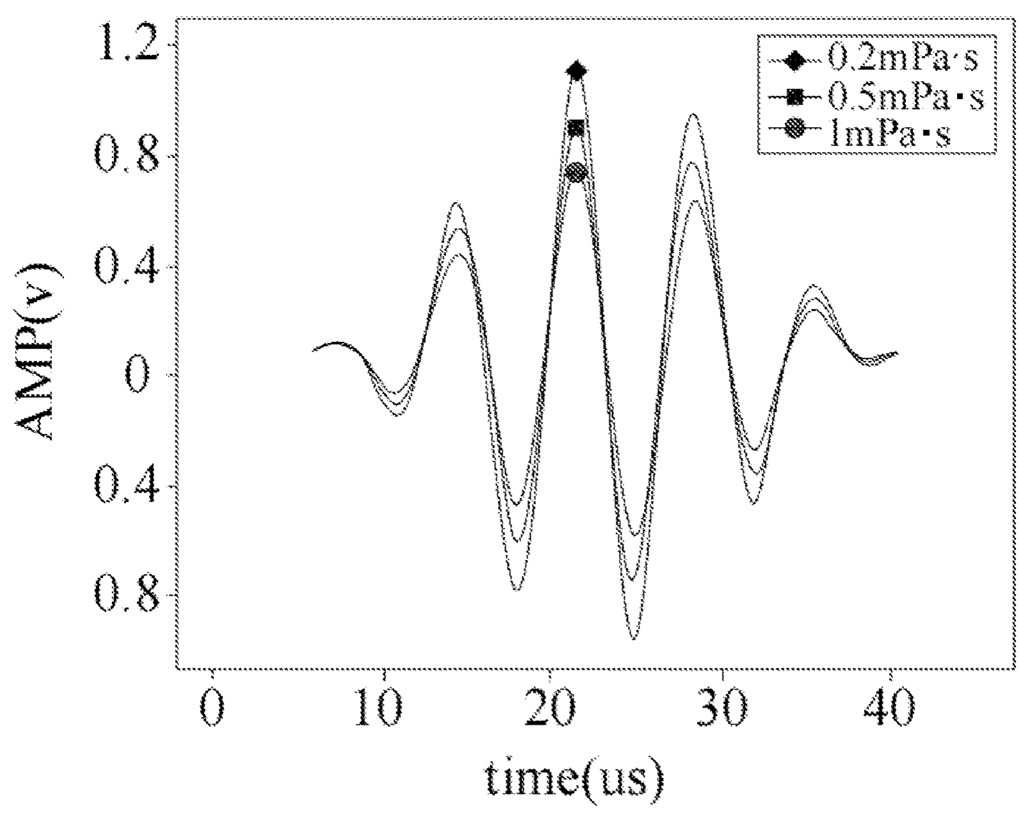

In the above experimental conditions, only the viscosity of the liquid column changes, and it can be seen from the dispersion curve that when the viscosity of blood increases, the dispersion curve tends to move to the right, that is, with the same excitation frequency, the modal guided wave velocity will be different, and along with the increase of the viscosity of blood, the guided wave velocity slightly decreases and the amplitude will be attenuated to a certain extent. According to the above experimental phenomena, the specific implementation method is determined as follows:

in the specific implementation method, 36° C. water is used as a solvent, a thickening agent is used as a solute, ten groups of liquids with different viscosities ranging from 0.1 mPa·s to 1 mPa·s are arranged by matching with a commercial standard viscometer, the echo speeds and amplitudes of blood samples with different viscosities are measured by using the detection device, as shown in FIGS. 3*b* and 3*c*, the ten groups of data are converted and then sent to an established linear regression model, the model is trained to analyze the relationship of the viscosity and the guided wave attenuation as well as the guided wave speed change, and the specific implementation method is shown in the embodiment.

The embodiment of the present disclosure are as follows:

(1) Taking a liquid-filled micro-fine aluminum tube with an inner diameter of 400 um, an outer diameter of 600 um, a density of 2800 kg/m$^3$, an elastic modulus of 7.3×e10 N/m$^2$ and a Poisson ratio of 0.33 for example, dispersion curves of the tube filled with liquids with different viscosities are drawn (FIG. 3*a*) to find an optimal excitation frequency point around 240 khz;

(2) Taking 36° C. water as a solvent, adding a proper amount of salt to simulate venous blood to enable the density of the venous blood to reach (1.05 g/cm$^3$), preparing ten parts of solution of hydroxyethyl cellulose (HEC) powder with the viscosity of 0.1 mPa·s to 1 mPa·s and one part of saline solution without hydroxyethyl cellulose (HEC) powder, respectively feeding the ten parts of solution and one part of saline solution into the aluminum tube, carrying out guided wave excitation, receiving and recording the velocity v and the amplitude a of guided wave received by saline, and the velocity v0-v9, a0-a9 of each solution for receiving the guided wave.

(3) For simplification of the regression model and elimination of the constant term, some processing is performed on the guided wave echo data, the first step: the guided wave velocity v is converted into a time of flight $TOF_{100}$:

$$TOF_{100}=200\times l/v$$

where $TOF_{100}$ refers to the time of flight of guided wave (the time when the micro-fine metal tube moves back and forth 100 times), and l is the length of the micro-fine metal tube.

The second step: taking the absolute value of the difference between the time $TOF_i$ of the guided wave echoes with different liquid filling viscosities 100 times and the guided wave echo $TOF_{100}$ of the water-filled pipeline as the absolute time of flight by using the following formula:

$$\Delta TOF=|TOF_i-TOF_{100}|.$$

The third step: converting the guided wave amplitude into an attenuation ratio by using the following formula:

$$w=1-AMP_i/AMP$$

wherein, $AMP_i$ represents amplitude of the guided wave echo at the i-th filling viscosity, and AMP represents the amplitude of the guided wave echo of the water filled pipeline.

Figure 4:
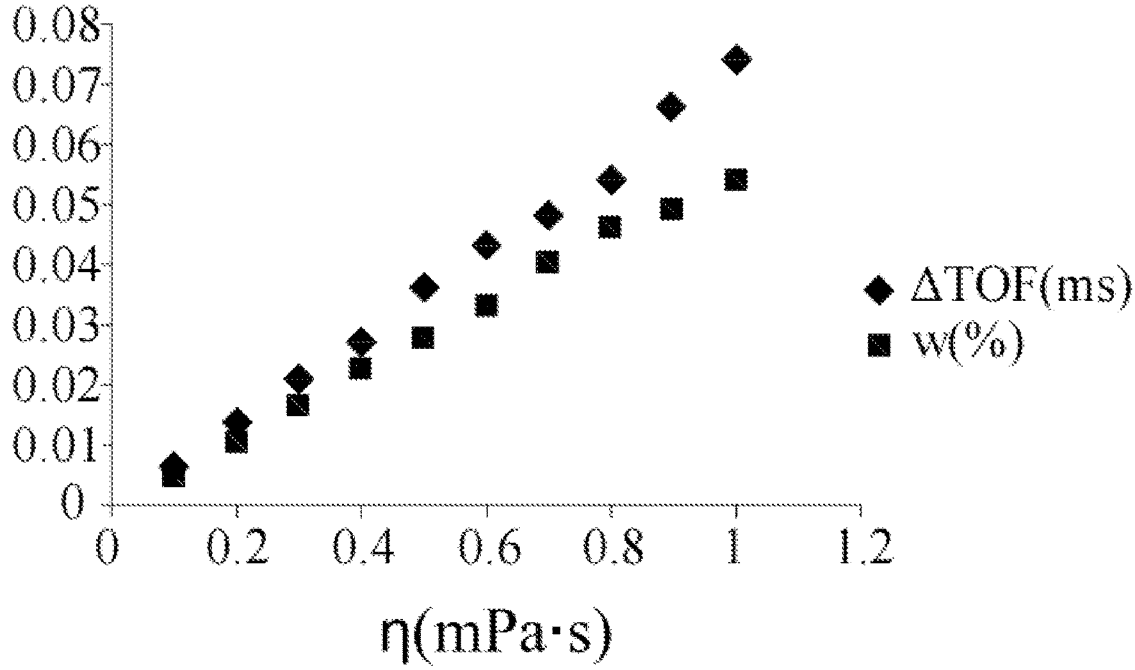
FIG. 4 is a graph showing the relationship of torsional guided wave echo TOF, W versus viscosity.

Through the above processing, when ΔTOF and w are 0, the viscosity is 0 equal to the viscosity of water, i.e., the linear regression equation constant term is eliminated. The resulting data are shown in FIG. 4.

(4) The first step is as follows: establishing a linear regression model:

$$\eta=k_1*\Delta TOF+k_2*w;$$

The second step: establishing a loss function by taking the mean square error as a reference:

$$J=\frac{1}{2m}\sum_{i=1}^{m}(h(x^i)-y^i)^2;$$

Figure 5A:
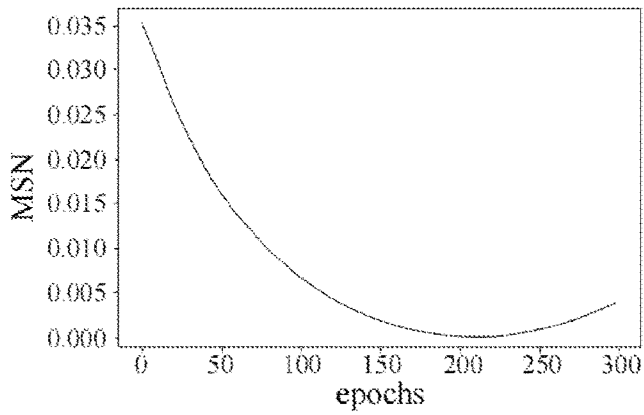
FIG. 5*a* is a training effect diagram of a viscosity prediction model.
Figure 5B:
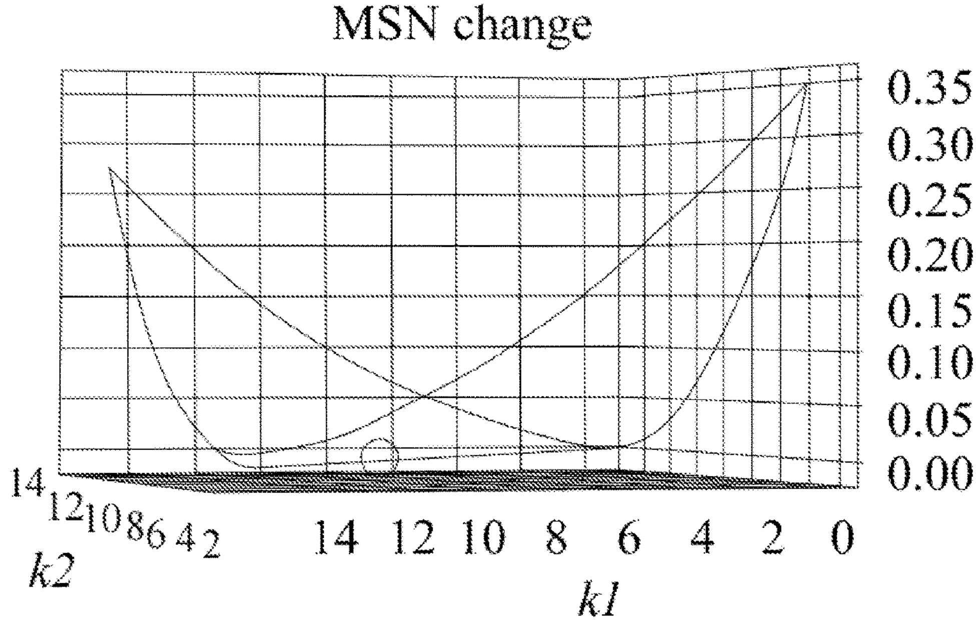
FIG. 5*b* is a diagram showing the results of model parameter calculation.

The third step: setting iteration round number and learning rate, solving the model by using a gradient descent method, which is a method combining self-adaptive gradient descent and momentum gradient descent, and as can be seen from FIG. 5*a*, after 300 rounds of training, the MSN (mean square error) of the model descends and then ascends, at the moment, overfitting occurs to the model, when the training round number is 212 rounds, the MSN descends to the lowest point $4*10^{-5}$, and finally solving parameters: k1=7.15, k2=8.81 and draw the MSN variation graph in FIG. 5*b* over the parameter point range, it can be seen that the parameters solved by the model do make the MSN reach a minimum value.

The fourth step: substituting the solved parameters into the original model and data, and comparing the predicted data with the real data, as shown in FIG. 5*a*, wherein the obtained errors are all in the range of one percent.

The part of device usage:

(1) The above method is converted into a code to be burnt into a main control unit of the device.

(2) The main control unit controls the blood micro-flow pump to send blood into the micro-fine metal tube by driving the micro-flow pump control module, when a blood sample is filled in the metal tube, the guided wave excitation unit receives a main control excitation signal and drives the transducer to generate ultrasonic guided waves, and the guided wave receiving unit sends the received signals into the main control unit for echo signal processing after filtering and amplifying the received signals.

(3) After calculating the parameters of ΔTOF and w of the echo, feeding the parameters into a trained model, and further obtaining the blood viscosity and displaying the blood viscosity on a display module.

(4) And then the main control unit controls the blood micro-flow pump to extract distilled water again to clean the inner tube of the device, and the primary blood viscosity detection is completed.

Therefore, the disclosure realizes the rapid and accurate measurement of the blood viscosity by utilizing the influence of the blood viscosity on the transmission characteristic of the ultrasonic guided wave and combining a detection method based on machine learning and taking a portable blood sampling device as a support, and the measurement error of the measurement method is within one percent by comparing with a commercial viscometer. The method realizes the rapid and accurate measurement of the blood viscosity of the human body, provides a new method for the dynamic change of perioperative blood viscosity parameters, namely the analysis of the thrombus elasticity and the requirement of minimally invasive rapid measurement of the blood viscosity in the daily health monitoring of the human body, and has remarkable technical effects.

The principle and the embodiment of the present disclosure are explained by applying specific examples, and the above description of the embodiments is only used to help understanding the method and the core idea of the present disclosure; meanwhile, for a person skilled in the art, according to the idea of the present disclosure, the specific embodiments and the application range may be changed. In conclusion, the contents of this specification should not be construed as limiting the present disclosure.

What is claimed is:

1. A device configured for detection of blood viscosity in a micro-fine metal tube based on a torsional guided wave, comprising a device shell, a blood sampling unit and a blood sampling electrical circuit, wherein the blood sampling unit and the blood sampling electrical circuit are arranged on the device shell and are electrically connected to each other;

the blood sampling unit comprises an external blood sampling module, a sample transportation pipeline, a micro-fine metal tube (5) and a blood pump (7), the sample transportation pipeline comprises a sample feeding tube (4) and a sample discharging tube (6), the sample feeding tube (4) and the sample discharging tube (6) are respectively arranged on two sides of the device shell, an inlet of the sample feeding tube (4) is communicated with the outside of the device shell and is used for being connected with the external blood sampling module, an outlet of the sample feeding tube (4) is communicated with an inlet of the blood pump (7) through the micro-fine metal tube (5), an outlet of the blood pump (7) is communicated with an inlet of the sample discharging tube (6), and an outlet of the sample discharging tube (6) is communicated with the outside of the device shell;

a magnetostrictive component is arranged outside the micro-fine metal tube (5), the magnetostrictive component comprises permanent magnets (17), a coil (18) and a magnetostrictive powder coating (19), the magnetostrictive powder coating (19) is coated on an outer surface of the micro-fine metal tube (5), the coil (18) is wound outside the magnetostrictive powder coating (19), and the permanent magnets (17) are symmetrically arranged on two sides outside the coil (18).

2. The device configured for detection of blood viscosity in the micro-fine metal tube based on the torsional guided wave according to claim 1, wherein the external blood sampling module comprises a sampling needle (2) and a blood sampling bag (3), the blood sampling bag (3) is connected with the sample feeding tube (4), and the blood sampling bag (3) is configured for sampling blood in veins of a human body through the sampling needle (2).

3. A method for detecting blood viscosity based on machine learning configured for the device of claim 2, wherein:

1) Calculating by a semi-analytic finite element method to obtain a dispersion characteristic curve of guided wave modal of the micro-fine metal tube (5) according to structural geometric parameters and material mechanics characteristic parameters of the micro-fine metal tube (5), and selecting guided wave excitation frequency according to the dispersion characteristic curve of guided wave modal;

2) Taking water at 36° C. as a solvent, using a thickening agent as a solute, preparing liquids with different concentrations to obtain liquids with different viscosities, and measuring the viscosities of the prepared liquids by using a commercial standard viscometer to obtain actual viscosities;

3) Filling liquid with different viscosities into the micro-fine metal tube (5), obtaining time of flight TOF and amplitude AMP of guided wave in the micro-fine metal tube (5) by acquiring and then processing echo signals under the guided wave excitation of T (0,1) of guided wave excitation frequency, and then calculating absolute time of flight ΔTOF and amplitude attenuation ratio w according to the time of flight TOF and amplitude AMP of guided wave;

4) Establishing a linear regression model among the absolute time of flight ΔTOF, the amplitude attenuation ratio w and the viscosity, predicting two input variables of the absolute time of flight ΔTOF and the amplitude attenuation ratio w by the linear regression model to obtain a predicted viscosity, establishing a loss function measurement according to a difference value between the predicted viscosity and the actual viscosity, and optimizing the model by using a gradient descent optimization method; and 5) Adding the blood sample into the micro-fine metal tube (5) under a condition of to be detected, repeating steps 3) and 4) to obtain the absolute time of flight ΔTOF and the amplitude attenuation ratio w, input the absolute time of flight ΔTOF and the amplitude attenuation ratio w into a linear regression model configured for processing and output an obtained viscosity, and optimize the model by using a gradient descent optimization method.

4. The method for detecting blood viscosity based on machine learning according to claim 3, wherein: in step 1), the guided wave modal is a T (0,1) modal guided wave.

5. The method for detecting blood viscosity based on machine learning according to claim 3, wherein: according to the dispersion characteristic curve of the micro-fine metal tube in the step 1), when the viscosity of filled liquid in the micro-fine metal tube (5) is increased, the dispersion curve displaces to the right, which indicates that with the same frequency, a propagation speed of a guided wave in an inner wall of the micro-fine metal tube (5) is higher when the viscosity of filled liquid is larger, and the time of flight TOF of the guided wave is shorter.

6. The method for detecting blood viscosity based on machine learning according to claim 3, wherein: the thickening agent in the step 2) is hydroxyethyl cellulose (HEC) powder.

7. The method for detecting blood viscosity based on machine learning according to claim 3, wherein: in the step 4), the linear regression model specifically is:

$$\eta = k_1 * \Delta TOF + k_2 * w$$

wherein k1 and k2 are a first model coefficient and a second model coefficient, and η represents viscosity;

the loss function uses the mean square error as the function return value, and is calculated as:

$$J = \frac{1}{2}\sum_{i=1}^{m}(h(x^i) - y^i)^2$$

wherein J represents the mean square error between the predicted viscosity and the actual viscosity, $h(x^i)$ is the predicted viscosity obtained by processing the absolute time of flight ΔTOF and the amplitude attenuation ratio w through the linear regression model, $y^i$ is the actual viscosity of the solution prepared by using a standard viscometer, i represents the ith part of HEC powder solution, and m represents the total parts of the HEC powder solution.

8. The device configured for detection of blood viscosity in the micro-fine metal tube based on the torsional guided wave according to claim 1, wherein the blood pump (7) and the coil (18) are connected to the blood sampling electrical circuit, and the blood sampling electrical circuit comprises a main control unit (8), a guided wave excitation unit (11), a pulse generation module (12), a power amplification module (13), an echo receiving unit (14), a pre-amplification module (15) and a data acquisition module (16); the main control unit (8) is connected with a display module (9), the main control unit (8) is connected with the blood pump (7) through a pump control module (10), the main control unit (8) is connected with two ends of the coil (18) through the guided wave excitation unit (11), the pulse generation module (12) and the power amplification module (13) in sequence, and the two ends of the coil (18) are connected with the main control unit (8) through the data acquisition module (16), the pre-amplification module (15) and the echo receiving unit (14) in sequence.

9. A method for detecting blood viscosity based on machine learning configured for the device of claim 3, wherein:

1) Calculating by a semi-analytic finite element method to obtain a dispersion characteristic curve of guided wave modal of the micro-fine metal tube (5) according to structural geometric parameters and material mechanics characteristic parameters of the micro-fine metal tube (5), and selecting guided wave excitation frequency according to the dispersion characteristic curve of guided wave modal;

2) Taking water at 36° C. as a solvent, using a thickening agent as a solute, preparing liquids with different concentrations to obtain liquids with different viscosities, and measuring the viscosities of the prepared liquids by using a commercial standard viscometer to obtain actual viscosities;

3) Filling liquid with different viscosities into the micro-fine metal tube (5), obtaining time of flight TOF and amplitude AMP of guided wave in the micro-fine metal tube (5) by acquiring and then processing echo signals under the guided wave excitation of T (0,1) of guided wave excitation frequency, and then calculating absolute time of flight ΔTOF and amplitude attenuation ratio w according to the time of flight TOF and amplitude AMP of guided wave;

4) Establishing a linear regression model among the absolute time of flight ΔTOF, the amplitude attenuation ratio w and the viscosity, predicting two input variables of the absolute time of flight ΔTOF and the amplitude attenuation ratio w by the linear regression model to obtain a predicted viscosity, establishing a loss function measurement according to a difference value between the predicted viscosity and the actual viscosity, and optimizing the model by using a gradient descent optimization method; and 5) Adding the blood sample into the micro-fine metal tube (5) under a condition of to be detected, repeating steps 3) and 4) to obtain the absolute time of flight ΔTOF and the amplitude attenuation ratio w, input the absolute time of flight ΔTOF and the amplitude attenuation ratio w into a linear regression model configured for processing and output an obtained viscosity, and optimize the model by using a gradient descent optimization method.

10. The method for detecting blood viscosity based on machine learning according to claim 9, wherein: in step 1), the guided wave modal is a T (0,1) modal guided wave.

11. The method for detecting blood viscosity based on machine learning according to claim 9, wherein: according to the dispersion characteristic curve of the micro-fine metal tube in the step 1), when the viscosity of filled liquid in the micro-fine metal tube (5) is increased, the dispersion curve displaces to the right, which indicates that with the same frequency, a propagation speed of a guided wave in an inner wall of the micro-fine metal tube (5) is higher when the viscosity of filled liquid is larger, and the time of flight TOF of the guided wave is shorter.

12. The method for detecting blood viscosity based on machine learning according to claim 9, wherein: the thickening agent in the step 2) is hydroxyethyl cellulose (HEC) powder.

13. The method for detecting blood viscosity based on machine learning according to claim 9, wherein: in the step 4), the linear regression model specifically is:

$$\eta = k_1 * \Delta TOF + k_2 * w$$

wherein k1 and k2 are a first model coefficient and a second model coefficient, and η represents viscosity;

the loss function uses the mean square error as the function return value, and is calculated as:

$$J = \frac{1}{2}\sum_{i=1}^{m}(h(x^i) - y^i)^2$$

wherein J represents the mean square error between the predicted viscosity and the actual viscosity, $h(x^i)$ is the predicted viscosity obtained by processing the absolute time of flight ΔTOF and the amplitude attenuation ratio w through the linear regression model, $y^i$ is the actual viscosity of the solution prepared by using a standard viscometer, i represents the ith part of HEC powder solution, and m represents the total parts of the HEC powder solution.

14. The device configured for detection of blood viscosity in the micro-fine metal tube based on the torsional guided wave according to claim 8, wherein the main control unit (8) arranges an original excitation pulse digital signal and then sends the digital signal to the guided wave excitation unit (11), the digital signal is converted into an analog signal by the pulse generation module (12), the analog signal is amplified by the power of the power amplification module (13) and then applied to a guided wave transducer formed by the coil (18) and the permanent magnets (17), and a guided wave signal is coupled to the micro-fine metal tube (5) by the guided wave transducer; when the guided wave transducer receives the echo of a guided wave, a received echo signal is sent to the main control unit (8) configured for data processing after passing the data acquisition module (16) and then being subjected to pre-amplification by the pre-amplification module (15) in sequence, and a result is displayed on the display module (9) after the viscosity is predicted by a detection method.

15. A method for detecting blood viscosity based on machine learning configured for the device of claim 14, wherein:

1) Calculating by a semi-analytic finite element method to obtain a dispersion characteristic curve of guided wave modal of the micro-fine metal tube (5) according to structural geometric parameters and material mechanics characteristic parameters of the micro-fine metal tube (5), and selecting guided wave excitation frequency according to the dispersion characteristic curve of guided wave modal;
2) Taking water at 36° C. as a solvent, using a thickening agent as a solute, preparing liquids with different concentrations to obtain liquids with different viscosities, and measuring the viscosities of the prepared liquids by using a commercial standard viscometer to obtain actual viscosities;
3) Filling liquid with different viscosities into the micro-fine metal tube (5), obtaining time of flight TOF and amplitude AMP of guided wave in the micro-fine metal tube (5) by acquiring and then processing echo signals under the guided wave excitation of T (0,1) of guided wave excitation frequency, and then calculating absolute time of flight ΔTOF and amplitude attenuation ratio w according to the time of flight TOF and amplitude AMP of guided wave;
4) Establishing a linear regression model among the absolute time of flight ΔTOF, the amplitude attenuation ratio w and the viscosity, predicting two input variables of the absolute time of flight ΔTOF and the amplitude attenuation ratio w by the linear regression model to obtain a predicted viscosity, establishing a loss function measurement according to a difference value between the predicted viscosity and the actual viscosity, and optimizing the model by using a gradient descent optimization method; and
5) adding the blood sample into the micro-fine metal tube (5) under a condition of to be detected, repeating steps 3) and 4) to obtain the absolute time of flight ΔTOF and the amplitude attenuation ratio w, input the absolute time of flight ΔTOF and the amplitude attenuation ratio w into a linear regression model configured for processing and output an obtained viscosity, and optimize the model by using a gradient descent optimization method.

16. A method for detecting blood viscosity based on machine learning configured for the device of claim 1, wherein:

1) Calculating by a semi-analytic finite element method to obtain a dispersion characteristic curve of guided wave modal of the micro-fine metal tube (5) according to structural geometric parameters and material mechanics characteristic parameters of the micro-fine metal tube (5), and selecting guided wave excitation frequency according to the dispersion characteristic curve of guided wave modal;
2) Taking water at 36° C. as a solvent, using a thickening agent as a solute, preparing liquids with different concentrations to obtain liquids with different viscosities, and measuring the viscosities of the prepared liquids by using a commercial standard viscometer to obtain actual viscosities;
3) Filling liquid with different viscosities into the micro-fine metal tube (5), obtaining time of flight TOF and amplitude AMP of guided wave in the micro-fine metal tube (5) by acquiring and then processing echo signals under the guided wave excitation of T (0,1) of guided wave excitation frequency, and then calculating absolute time of flight ΔTOF and amplitude attenuation ratio w according to the time of flight TOF and amplitude AMP of guided wave;
4) Establishing a linear regression model among the absolute time of flight ΔTOF, the amplitude attenuation ratio w and the viscosity, predicting two input variables of the absolute time of flight ΔTOF and the amplitude attenuation ratio w by the linear regression model to obtain a predicted viscosity, establishing a loss function measurement according to a difference value between the predicted viscosity and the actual viscosity, and optimizing the model by using a gradient descent optimization method; and
5) adding the blood sample into the micro-fine metal tube (5) under a condition of to be detected, repeating steps 3) and 4) to obtain the absolute time of flight ΔTOF and the amplitude attenuation ratio w, input the absolute time of flight ΔTOF and the amplitude attenuation ratio w into a linear regression model configured for processing and output an obtained viscosity, and optimize the model by using a gradient descent optimization method.

17. The method for detecting blood viscosity based on machine learning according to claim 16, wherein: in step 1), the guided wave modal is a T (0,1) modal guided wave.

18. The method for detecting blood viscosity based on machine learning according to claim 16, wherein: according to the dispersion characteristic curve of the micro-fine metal tube in the step 1), when the viscosity of filled liquid in the micro-fine metal tube (5) is increased, the dispersion curve displaces to the right, which indicates that with the same frequency, a propagation speed of a guided wave in an inner wall of the micro-fine metal tube (5) is higher when the viscosity of filled liquid is larger, and the time of flight TOF of the guided wave is shorter.

19. The method for detecting blood viscosity based on machine learning according to claim 16, wherein: the thickening agent in the step 2) is hydroxyethyl cellulose (HEC) powder.

20. The method for detecting blood viscosity based on machine learning according to claim 5, wherein: in the step 4), the linear regression model specifically is:

$$\eta = k_1 * \Delta TOF + k_2 * w$$

wherein k1 and k2 are a first model coefficient and a second model coefficient, and η represents viscosity;

the loss function uses the mean square error as the function return value, and is calculated as:

$$J = \frac{1}{2}\sum_{i=1}^{m}(h(x^i) - y^i)^2$$

wherein J represents the mean square error between the predicted viscosity and the actual viscosity, $h(x^i)$ is the predicted viscosity obtained by processing the absolute time of flight ΔTOF and the amplitude attenuation ratio w through the linear regression model, $y^i$ is the actual viscosity of the solution prepared by using a standard viscometer, i represents the ith part of HEC powder solution, and m represents the total parts of the HEC powder solution.

* * * * *